United States Patent [19]
Bell et al.

[11] Patent Number: 5,714,640
[45] Date of Patent: Feb. 3, 1998

[54] VAPOR POCKET REACTOR

[75] Inventors: Weldon K. Bell, Pennington; Stephen H. Brown, Princeton; Frederick E. Daugherty, Gibbstown, all of N.J.; Mohsen N. Harandi, Langhorne; Jeffrey C. Trewella, Kennett Square, both of Pa.

[73] Assignee: Mobil Oil Corporation, Fairfax, Va.

[21] Appl. No.: 184,537

[22] Filed: Jan. 21, 1994

[51] Int. Cl.$^6$ ..................................................... C07C 41/00
[52] U.S. Cl. ................................................ 568/697; 202/152
[58] Field of Search ............................... 568/697; 202/152

[56] References Cited

U.S. PATENT DOCUMENTS

| | | | |
|---|---|---|---|
| 3,119,766 | 1/1964 | Voltz et al. | 208/291 |
| 3,556,737 | 1/1971 | Boyd | 23/288 |
| 4,215,011 | 7/1980 | Smith, Jr. | 252/426 |
| 4,232,177 | 11/1980 | Smith, Jr. | 585/324 |
| 4,242,530 | 12/1980 | Smith, Jr. | 585/510 |
| 4,250,052 | 2/1981 | Smith, Jr. | 252/426 |
| 4,302,356 | 11/1981 | Smith, Jr. | 252/426 |
| 4,306,068 | 12/1981 | Smith, Jr. | 546/184 |
| 4,307,254 | 12/1981 | Smith, Jr. | 568/697 |
| 4,332,968 | 6/1982 | Smith, Jr. | 564/278 |
| 4,336,407 | 6/1982 | Smith, Jr. | 568/697 |
| 4,375,576 | 3/1983 | Smith, Jr. | 585/510 |
| 4,439,350 | 3/1984 | Jones, Jr. | 502/527 |
| 4,443,559 | 4/1984 | Smith, Jr. | 502/527 |
| 4,447,668 | 5/1984 | Smith, Jr. et al. | 585/639 |
| 4,471,154 | 9/1984 | Franklin | 585/864 |
| 4,475,005 | 10/1984 | Paret | 568/697 |
| 4,482,775 | 11/1984 | Smith, Jr. | 585/671 |
| 4,504,687 | 3/1985 | Jones, Jr. | 568/697 |
| 4,510,336 | 4/1985 | Hearn | 568/697 |
| 4,536,373 | 8/1985 | Jones, Jr. | 422/211 |
| 4,551,567 | 11/1985 | Smith, Jr. | 568/907 |
| 4,597,947 | 7/1986 | Almaula | 422/191 |
| 4,624,748 | 11/1986 | Haunschild | 203/29 |
| 4,847,430 | 7/1989 | Quang et al. | 568/697 |
| 4,847,431 | 7/1989 | Nocca et al. | 568/197 |
| 4,925,455 | 5/1990 | Harandi et al. | 44/77 |
| 4,950,803 | 8/1990 | Smith, Jr. et al. | 568/697 |
| 5,013,407 | 5/1991 | Nocca et al. | 202/158 |
| 5,026,459 | 6/1991 | Quang et al. | 202/158 |
| 5,057,468 | 10/1991 | Adams | 502/1 |
| 5,059,733 | 10/1991 | Sweeney | 585/324 |
| 5,073,236 | 12/1991 | Gelbein et al. | 203/29 |
| 5,108,550 | 4/1992 | Pinaire et al. | 203/1 |
| 5,130,102 | 7/1992 | Jones, Jr. | 422/191 |
| 5,176,883 | 1/1993 | Smith, Jr. et al. | 422/211 |
| 5,177,289 | 1/1993 | Smith, Jr. et al. | 585/526 |
| 5,189,001 | 2/1993 | Johnson | 502/159 |
| 5,204,064 | 4/1993 | Smith, Jr. | 422/106 |
| 5,235,102 | 8/1993 | Palmer et al. | 562/607 |
| 5,243,102 | 9/1993 | Marker et al. | 568/697 |
| 5,248,836 | 9/1993 | Bakshi et al. | 568/697 |
| 5,248,837 | 9/1993 | Smith, Jr. et al. | 568/697 |

FOREIGN PATENT DOCUMENTS

| | | | |
|---|---|---|---|
| 9408679 | 4/1994 | WIPO | B01D 3/00 |
| 9408681 | 4/1994 | WIPO | B01D 3/32 |
| 9408682 | 4/1994 | WIPO | B01D 3/32 |

OTHER PUBLICATIONS

Autoclave Catalytic Reactor Selection Guide, by Autoclave Engineers, Inc., Erie, Pa., 8 pgs, coded "AHA MC 1187 8M", (1987).

*Primary Examiner*—Shean C. Wu
*Attorney, Agent, or Firm*—Malcolm D. Keen; Thomas W. Steinberg

[57] ABSTRACT

A condensation reaction process and reactor for converting a plurality of reactants to at least one reaction product having a vapor pressure less than the vapor pressure of the reactants. The process includes heating a liquid phase of the reactants to at least partial vaporization thus forming a vapor phase of the reactants. The vapor phase reactants are passed in a vapor and or condensed state through at least one catalyst bed spaced from the liquid state to form reaction product(s). The reaction product(s) is returned to the liquid phase without additional contact with catalyst.

26 Claims, 7 Drawing Sheets

TAME Equilibrium vs. Temperature

MeOH Enrichment Ratio vs. Wt% MeOH 5,714,640

VAPOR POCKET REACTOR

BACKGROUND OF THE INVENTION

1. Field of the Invention

The present invention relates to a method of and a reactor for converting at least one reactant to at least one reaction product having a vapor pressure less than the vapor pressure of the reactant(s). More particularly, the present invention relates to a method of and a reactor for improving conversion in equilibrium limited reactions, and for improving selectivities in condensation reactions.

2. Description of the Prior Art

It is known to use catalytic distillation processes for oligomerization and etherification of $C_4$ and $C_5$ iso-olefins. The process consists of concurrent reaction and distillation in a combination reactor-distillation column. A catalytic distillation process is disclosed in U.S. Pat. Nos. 4,215,011 and 4,232,177.

It is also known to prepare tertiary alkyl ethers, particularly methyl tertiary butyl ether (MTBE) and tertiary amyl methyl ether (TAME) by reacting an iso-olefin, typically in a hydrocarbon fraction, with an alcohol, such as methanol, in the presence of an acid catalyst, for example sulfuric acid, hydrofluoric acid, aluminum chloride or boron fluoride. As disclosed in U.S. Pat. No. 4,605,787, acidic zeolite catalysts are also useful in these processes. Other suitable catalyst are carbonaceous materials containing —$SO_3H$ groups, for example sulfonated coals, sulfonated phenol-formaldehyde resins, sulfonated coumarone-indene polymers or sulfonated polystyrene-divinylbenzene resins.

The catalytic distillation (catstill) process provides for both reaction and distillation concurrently in the same vessel and at least in part within the catalyst bed in the vessel. For example, in the catstill process, methanol and an isobutene-containing $C_4$ stream are continuously fed to the reactor-distillation column where they are contacted in the catalyst section of the column. The methanol preferentially reacts with isobutene, forming MTBE, which is less volatile than the $C_4$ components of the feed and the methanol. Hence the MTBE drops in the column to form the bottoms. However, the MTBE product returns to the liquid stream flowing downwardly through successive beds of catalyst and thus is subject to further catalytic reactions. Concurrently, unreacted $C_4$ (e.g. n-butane, n-butenes) are more volatile than MTBE and form an overhead. Since the reaction is reversible, conversion will be limited in part because of MTBE product contacting catalyst. However, by removing the MTBE as a bottoms from contact with the catalyst, the reaction is forced to completion in accordance with Le Chatelier Principle. Therefore the process can provide high conversion of isobutene and methanol reactants.

The catalyst in a catstill performs both a reaction and a distillation function. The mass-transfer characteristics of a reactive distillation unit are critical because the unit must contribute to the vapor and liquid mass transfer. In order to affect efficient separation, the catalyst of a catstill must be in contact with the feedstock or bulk liquid phase.

Further, multi-reaction zone catstills are limited to reacting materials with similar volatilities. Because the catstill is an open continuous flow distillation system, reactants with different volatilities separate and stratify into different regions of the distillation tower. However, the reactants must be mixed to react. Therefore such units are limited to feeds having similar volatilities.

In addition, balancing reaction rates with distillation rates introduces further complexity. Operation, construction, and maintenance of a catstill unit is a challenging undertaking. The reaction rate and separation rate must be balanced. Each time a new reaction is run, a search must be made for the appropriate reaction temperature and pressure, and an appropriate reflux ratio and column height to maintain good mixing of the reagents in the reaction zone. At all times, care must be taken to avoid column fooding.

An object of the present invention is to provide a method of and reactor for driving equilibrium limited reactions.

Another object of the invention is to improve selectivities in condensation reactions in which the product(s) is reactive.

Yet another objective of the invention is to improve the operability by decoupling reaction and separation.

SUMMARY OF THE INVENTION

In accordance with a broad aspect of the present invention there is provided a reaction process for converting at least one reactant to at least one reaction product having a vapor pressure less than the Vapor pressure of the reactant(s). The process comprises the steps of heating a liquid phase comprising the reactant(s) to partial vaporization thus forming a vapor phase of the reactant(s), and passing the vapor phase reactant(s) in a vapor and/or condensed state through at least one catalyst bed separated from the liquid phase to form at least one condensed reaction product. The product(s) is returned to the liquid phase without additional contact with catalyst.

Thus, with a plurality of reactants, the vapor phase determines the composition of the reactants in the catalyst bed which is different than the composition of the liquid phase feed to the reactor.

The reactant(s) are refluxed between the liquid phase and the vapor phase until a desired concentration of the product(s) is in the liquid phase. The product(s) tends not to return to the vapor phase because of its lower vapor pressure. In this way the products are removed from further contact with catalyst and therefore from further reactions.

In accordance with another broad aspect of the present invention, there is provided a reactor for converting at least one reactant to at least one reaction product having a vapor pressure less than the vapor pressures of the reactant(s). The reactor comprises means for heating a liquid phase comprising the reactant(s) to partial vaporization thus forming a vapor phase of the reactant(s), and means including at least one catalyst bed separated from the bulk liquid phase for converting the reactant(s) to the product(s). Also included are means for passing the reactant(s) in a vapor and/or condensed state through the catalyst bed, and means for returning the product(s) to the liquid phase without additional contact with catalyst.

The vapor pocket reactor (VPR) of the present invention has significant advantages over a catstill. The present invention is useful for driving equilibrium-limited reactions and for obtaining good selectivities in condensation reactions in which the products are as reactive or are more reactive than the starting materials. Embodiments of the VPR provide a relatively simple process which does not require bulk separation of product from the reactants with recycle of the reactants. The VPR thus permits optional batch operation not available in the prior art.

The invention contemplates a batch embodiment, and an advantage of the batch embodiment is that reactants even of widely different volatilities remain in the reaction zone. Thus, the VPR can make good use of the greater volatility of propylene vs. water for IPA and DIPE synthesis.

Examples of reactants having widely different volatilities are propylene plus water to form isopropyl alcohol (IPA) and di-isopropyl (DIPE), and propylene plus benzene to form cumene also have large volatility differences. In these reactions propylene boils at −42° C., water at 100° C. and benzene at 80° C. In prior art catstills, it is difficult to mix propylene and water in the catalyst bed because propylene tends to rapidly exit the reactor with the raffinate and water goes to the bottoms. However, in specific aspects of the present invention there are provided batch and continuous reactor designs which force these reactants together on the catalyst to form the intended products.

Thus, the VPR can make good use of the greater volatility of propylene vs. water for IPA and DIPE synthesis. High conversions of propylene are obtained because the reaction zone is both enriched in propylene and depleted in IPA and DIPE giving conversion both a Le Chatelier push, due to increased propylene/water on the catalyst, and a pull, due to reduced IPA and DIPE/reactants on the catalyst Another advantage of the embodiments of the present invention is that they improve the productivity of the catalyst system. The heavy product formed in each catalytic zone quickly leaves that zone, and as a liquid is not again exposed to the catalyst. In a batch embodiment of the invention, reaction product falls to the bulk liquid zone; and in the multi-stage embodiments the product is captured in the liquid reflux which bypasses the rest of the catalytic zones. Thus, the chance of reverse reaction occurrence is minimized and reaction equilibrium is shifted toward the product.

Therefore, the VPR drives equilibrium-limited reactions, and protects reactive products. A number of commodity fuel components and petrochemicals are products of equilibrium-limited reactions or could benefit from product protection provided by the method and reactor of the present invention. These include but are not limited to alkylation, MTBE, TAME, di-isopropyl ether (DIPE), propylene and butene hydration, aldehyde condensation, aldol condensation, ketone alkyl-silylation, ester synthesis from acids and olefins, and alcoholysis of dialkyl dichlorosilanes.

In the VPR, the catalyst performs only one function, that of catalysis. The sole function of the catalyst is to convert the reactants defined by the vapor phase. Mass transfer is achieved by boiling and condensing. Thus, catalyst contact with the feedstock bulk liquid and reaction products therein is avoided in all the embodiments, except a continuous VPR system, where fresh makeup feed contact with catalyst is minimized by premixing such feed with large multiples of condensate. Furthermore, as in all other embodiments, reaction product(s) of the continuous VPR system, is quickly removed from the catalyst bed to avoid further reaction involving the product(s).

Further, the invention permits the use of a batch reactor. The batch VPR is simple to build and easy to operate. It is operated by loading catalyst and reactants, sealing, bringing to temperature, and turning on condenser coolant. The reactions can be run over a wide range of temperature without concern. The reactor pressure automatically adjusts to the combined vapor pressures of the reactor contents without large changes in reaction zone composition.

In addition to condensation reactions, the process and system of the present invention are particularly useful for the following reactions; alkylation, e.g. olefin/aromatic and olefin/isoparaffin to make ethyl benzene and gasoline alkylate; dimerization; etherification; hydration; rearrangements which reduce vapor pressure; and isomerization, e.g. ketone to enol. The invention requires only that the reactant(s) are partially vaporized in the reaction and that the product has a vapor pressure less than the vapor pressure of the reactant(s).

As used herein, "without additional contact with catalyst" means that the product(s) once in a liquid state is returned to the liquid phase, and that the returning liquid does not contact the catalyst bed. The definition contemplates that a minimal amount of reaction product typically will be revaporized and therefore will again contact the catalyst bed. However, this minimal product contact with the bed will not significantly affect equilibrium or reactant conversion.

DESCRIPTION OF SPECIFIC EMBODIMENTS

Batch VPR with Liquid Feed to Catalyst

Figure 1:
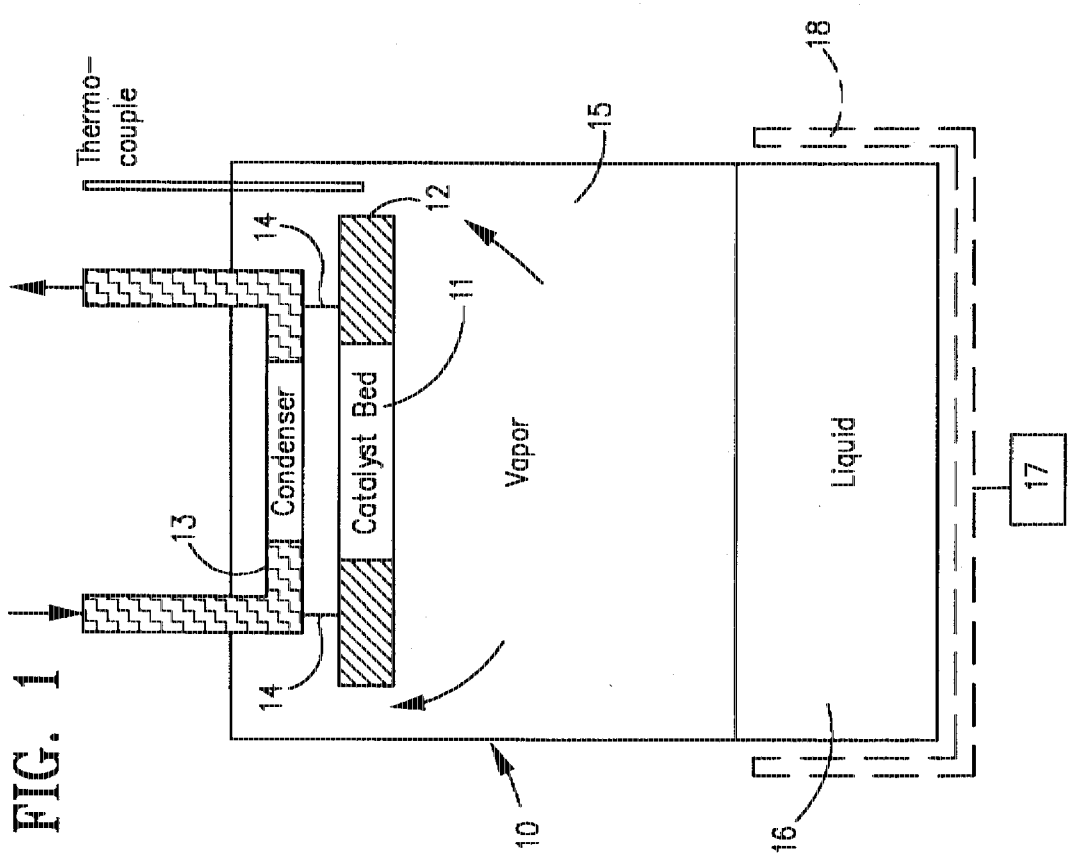
FIG. 1 is a schematic drawing of a batch reactor embodiment of the present invention with the reactants contacting the catalyst in a liquid state.

With reference to FIG. 1, there is shown a schematic of a single stage VPR embodiment of the present invention in the form of a batch reactor 10. A modified Parr autoclave is suitable as a lab embodiment of the batch reactor 10. A catalyst bed 11 is suspended in a screened holder 12 directly beneath a condenser 13 by a pair of arms 14. Alternatively, the catalyst bed may be supported in any suitable structure which permits fluid passage therethrough to contact the catalyst. For example, the support structure may be in the form of permeable plate arrays as disclosed in U.S. Pat. No. 5,073,236, or a foraminous horizontal support.

Thus, the catalyst bed 11 is located in a vapor zone 15 of the reactor and not in the liquid reactant zone 16 at the bottom of the reactor as is normally done in a batch reactor. The VPR takes advantage of an ability in accordance with the invention to position a heterogeneous catalyst in the vapor zone 15, hence the name Vapor Pocket Reactor (VPR).

Another advantage of placing the catalyst in the vapor zone 15 is that the composition of the reactants in the catalyst bed are determined by the composition of the vapor phase and not by the composition of the liquid phase 16. To initiate the reaction, the catalyst 11 is suspended in the vapor zone 15 beneath the condenser 13. Then the reactor 10 is sealed or closed, and coolant such as water is flowed through the condenser 13.

A controller 17 is attached to a heating mantle 18 in which the reactor 10 is positioned. The controller 17 is set to apply heat to the liquid portion 16 until the reactor 10 reaches a predetermined temperature at which time the reactants are partially vaporized. Also, water is fed through the condenser 13 such that heat is removed by the condenser 13 at the rate at which the mantle 18 is supplying heat to thereby balance the input and the output of heat. Obviously, a small amount of heat is also lost via radiative cooling which can be minimized with insulation. Further, heat is also supplied or removed by the reactions.

In the FIG. 1 batch embodiment, the vapor travels upwardly and around the catalyst bed 11 through the space between the bed and the interior walls of the reactor 10. This occurs because the pressure drop across the catalyst bed causes the vapor to take the path of least resistance around the bed from the liquid source 16 of vapor at the bottom of the reactor 10 to the condenser 13 which is the sink for the vapor. Thus, reflux is generated. For every gram of condensate formed by the condenser 13, one gram of liquid evaporates from the bulk liquid 16 at the bottom of the reactor 10. Therefore, if a large amount of heat energy is applied to the reactor 10, the bulk liquid at the bottom will boil forming a stream of vapor moving up around the catalyst bed 11 to the condenser 13 where a condensate stream of reactants is formed which trickles downwardly through the catalyst bed 11 to be converted into reaction product. The product then drips from the catalyst bed down to the bulk liquid 16 at the bottom of the reactor 10.

For a given surface area condenser 13, increasing the flow rate of water through the condenser 13 will increase the rate at which heat is removed, and the increase in heat removal rate calls for more heat to be applied. The increase in applied heat increases the rate at which the liquid is turned into vapor. This action increases the flux of the condensate across the catalyst bed. Thus, to circulate the feed across the catalyst, the liquid is heated and the vapor is cooled. This serves to reflux the system by vaporizing the liquid and condensing the vapor to provide a steady stream of condensate as fresh feed to the catalyst bed.

In this embodiment, the catalyst feed is condensate. In another batch reactor to be described with reference to FIG. 2, and in continuous reactor embodiments to be described with reference to FIGS. 5 and 7, the feed to the catalyst beds is in a vapor state. Thus, the feed to the catalyst bed can be liquid (condensate) and/or vapor. However, an important aspect of the invention is that the composition of the catalyst feed is at least predominately determined by the vapor phase, and not by the liquid feed (phase) to the reactor. Therefore, the feed to the catalyst is not the feed to the reactor.

BATCH VPR WITH VAPOR FEED TO CATALYST

Figure 2:
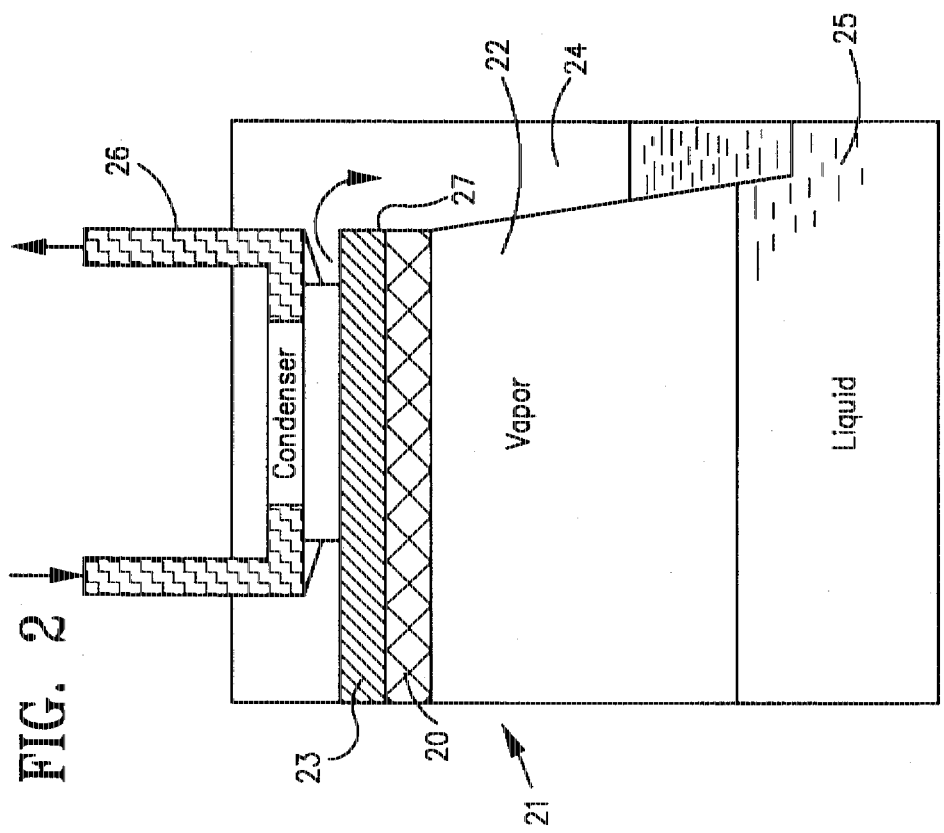
FIG. 2 is schematic drawing of another batch reactor embodiment of the invention with the reactants contacting the catalyst in a vapor state.

FIG. 2 shows another embodiment of a batch reactor where a bed of catalyst 20 is extended out to the wall on one side of the reactor 21, and is suspended below a bubble-cap tray 23. Heat is applied to the bulk liquid 25 as in FIG. 1 to form a vapor phase in the vapor zone 22. The vapor rises though the catalyst bed 20 forming product(s) therein, and through the tray. The product(s) is condensed by heat exchange action of a condenser 26, and falls back on the bubble-cap tray 23. Liquid on the tray 23 flows over a wier 27, down a downcomer 24 to the bulk liquid 25 at the bottom of the reactor 21. The downcomer 24 extends down into the bulk liquid 25 and provides a pressure drop across the catalyst bed so that the vapor is forced upwardly through the catalyst bed 20.

The major benefits of reactors designed in accordance with the present invention are twofold. First, selectivity of condensation reactions is improved in a reaction where reactants A go to product B which can go to product C, and it is desired to concentrate product B. A typical example is olefin oligomerization where it is desired to convert a monomer to a dimer. The reactors of this invention prevent the dimer from further reaction to higher oligomers or isomers or decomposition product, because the dimer once formed does not again come into contact with catalyst. The dimer like other condensation products being of higher molecular weight will have a significantly reduced vapor pressure vs. the monomer. Therefore, the concentration of dimer product in the vapor phase is reduced significantly compared to that of the monomer (reactant). The first product formed has a lower vapor pressure and substantially all remains in the liquid phase. The higher the molecular weight of the monomer (reactants), the more dramatic the difference in vapor pressure. Therefore, the product is more efficiently isolated from the catalyst. This action shifts the equilibrium further towards the condensation product, as well as preventing further reaction of condensed material. In a selective conversion process, it is desirable to operate at or near reaction conditions for 100% conversion. Thus, the invention provides a form of product protection because once product is condensed into the liquid phase, the product does not return to the reaction zone.

Alkylation is an example of a reaction whose selectivity can be improved by VPR processing. An important measure of alkylation product quality is the trimethyl pentane:dimethylhexane (T/D) ratio. A second important product quality measure is the $C_9+$ yield. The undesirable products are $C_9+$ and dimethylhexanes. Both are products which can be made by secondary reactions of the primary product trimethylpentanes. In the VPR, the trimethylpentanes are removed upon formation, reducing the formation of dimethylhexanes and $C_9+$.

The second general class of reactions benefitted by the present invention are equilibrium condensation reactions in which the amount of reagents going to product is limited by thermodynamics, for example, the TAME reaction. The invention optimizes these reactions by increasing the concentration of the reactants and decreasing the concentration of the product in the catalyst bed. This is achieved by the reactants in the vapor phase being enriched by the light materials and depleted of the condensed materials. Thus, equilibrium-limited condensation reactions will obtain higher conversion of reactants to desired product.

CONTINUOUS VPR WITH LIQUID FEED TO CATALYST

Figure 3:
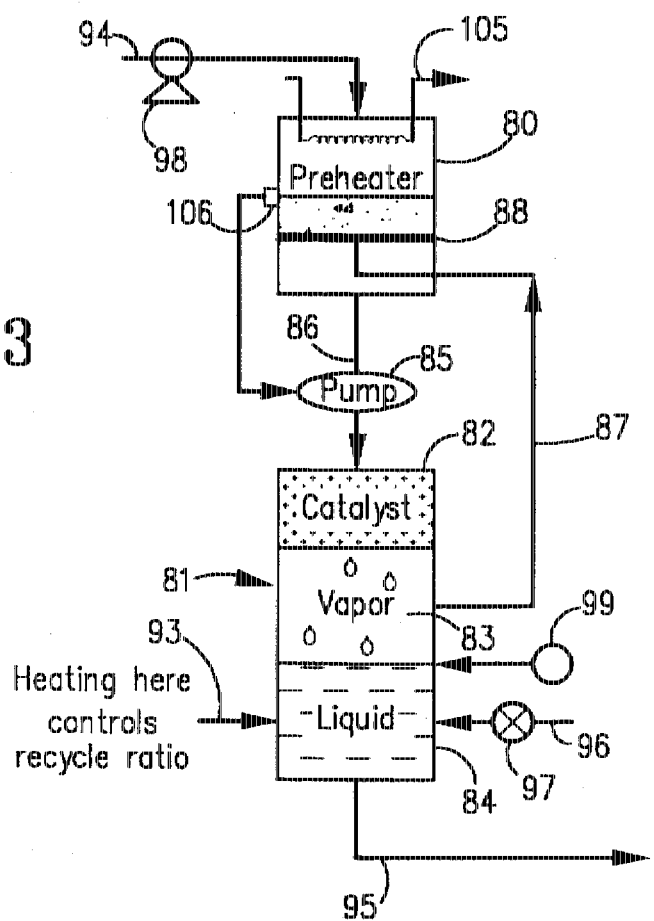
FIG. 3 is a schematic representation of a continuous reactor system embodiment of the invention with the reactants contacting the catalyst in a liquid state.

With reference to FIG. 3, there is shown a continuous VPR which is functionally similar to FIG. 1 embodiment. As discussed above, the essential elements of the batch VPR embodiment of FIG. 1 include a condenser 13, a catalyst bed 11, a vapor space 15 and a liquid phase 16. In the FIG. 3 embodiment, a preheater 80 functionally corresponds to the condenser 13 of FIG. 1, and a reactor 81 also has a catalyst bed 82, a vapor space 83, and a liquid phase 84.

Feed is initially charged to the reactor 81 by a line 96. When the liquid phase of reactants 84 is at a predetermined level, a valve 97 is closed, and heat is applied to the lower end 93 of the reactor to form the vapor phase 83. Heat may be applied by any of several known systems, such as a steam jacket or reboiler at the lower end 93 of the reactor. A booster pump 85 is provided in a line 86 for maintaining a positive pressure on the catalyst bed 82 to prevent the vaporized reactants in the vapor space 83 from entering the catalyst bed 82. Heat applied to the liquid 84 produces more vapor which is forced out of the reactor 81 via a line 87 to the feed preheater 80 where the vapor is fed through a vapor distributor 88, such as a bubble cap tray, and condensed by the condenser 105 or by direct heat exchange with liquid makeup feedstock fed to the preheater 80 by a line 94 and a pump 98. The condensed reactants in the feed preheater 80 are passed to the top of the catalyst bed 82 by the pump 85 where the reactants trickle through the bed and form product which drips down to the liquid phase 84.

The vapor stream in the vapor pumparound line 87 is fed to the feed preheater 80 at rate such that the weight ratio of recycle vapor to liquid makeup feed in the preheater 80 is from about 1:1 to about 100:1, preferably from about 2:1 to about 20:1. A suitable ratio is 10:1, by weight, such that the condensed vapor is dominant when the condensed vapor and feed mixture passes through the catalyst bed. Product formed in the catalyst bed 82 falls into the liquid phase to be removed by a product stream line 95. Thus, the system of FIG. 3 significantly reduces further reaction with the product to a minimal level, and also drives equilibrium-limited reactions to the desired product. The amount of feed to the preheater 80 though line 94 and pump 98 is controlled to makeup for product removed by line 95, and thus maintains a desired liquid level in the reactor 81. The fresh feed pump 98 and a product pump 100 work together to maintain an overall throughput. The pump 99 sets the overall reactor system hydrocarbon inventory. The reboiler 93 and the booster pump 85 work together to control reflux by maintaining a desired liquid level in the preheater 80.

Heat 93 applied to the liquid phase 84 of the reactor 81 controls the recycle weight ratio of vapor pumped around line 87 to liquid makeup feed 94 to the preheater 80. Increasing the amount of heat applied to the liquid will increase the amount of vapor. It should be noted that at a fixed pressure, the reactor is a constant temperature device. All heat applied to the reactor 81 is transferred into vaporization and increases recycle ratio.

As in the batch VPR embodiments, reactor temperature and pressure are linked in the continuous VPR. In order to change the temperature of the reactor, the pressure of the reactor must be changed. Changing temperature requires a change in pressure. Thus, without a pressure change, if more or less heat is applied to the liquid phase in the reactor, reflux by vaporization and condensation will increase or decrease without changing the temperature in the reactor.

In operation, the liquid phase is initially filled to a predetermined level, and the liquid level controller maintains the predetermined level by controlling the makeup feed and/or the rate of product removal from the reactor. For example, if the rate of feed is reduced, the liquid level controller will automatically slow the rate of product withdrawal to maintain the predetermined level. It should be noted that, with other conditions constant, the slower the rate of feed and product withdrawal, the higher the reflux ratio and the closer operation will be to equilibrium or complete reactant conversion.

In a TAME catalytic distillation reaction in a catstill, a $C_5$ feedstock containing $C_5$ paraffins, $C_5$ linear olefins and reactive isoamylenes is converted into TAME as a bottoms product. $C_5$ paraffins and unreactive $C_5$ linear olefins and unconverted isoamylenes and methanol exit as an overhead or TAME raffinate. Generally, all the TAME raffinate and TAME product are blended back together in the gasoline pool, with TAME providing octane enhancement. In comparison, the VPR embodiment of FIG. 3 simply takes the typical $C_5$ feedstock and processes it to provide a single TAME product stream 95 for the gasoline pool without the need for recombining reactor-separated streams. However, depending upon reaction conditions, methanol may be separated from the product stream 95 for recycle to the system.

Figure 4:
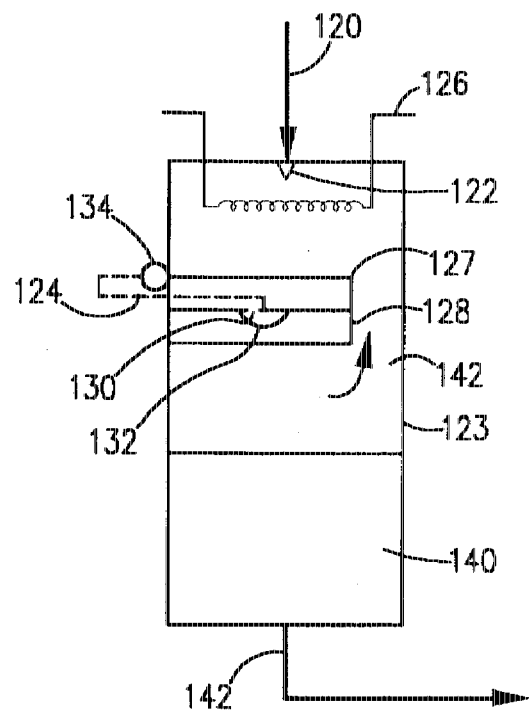
FIG. 4 is another continuous reactor system embodiment, also with the reactants contacting the catalyst in a liquid state.

With reference to FIG. 4, there is shown a continuous reactor system embodiment wherein the reactant(s) contact the catalyst bed 128 in a liquid phase. A liquid feedstock of reactants is passed by a line 120 through a nozzle 122 to the top of a reactor 123. The reactor has a tray 124 with a wier 126 at one side thereof. The cold feed and spray from the nozzle acts as a condenser. If additional condensation is desired, for example to increase recycle ratio, a typical heat exchanger condenser 126 can be used. The tray 124 has an opening 130 with a booster pump 132 therein. A liquid level controller 134 monitors the level of liquid in the tray 124 and prevents spill over the wier 126 by controlling the pump 132. Heat is applied to the reactor 124 as described with reference to FIG. 3. The pump 132 maintains a positive pressure on the top of the catalyst bed 128. Reactants are partially vaporized from the liquid phase 140, and pass upwardly through the opening 142 defined by the side of the bed 128 and the wier 126. The vapor phase mixes with the fresh feed spray from the nozzle, condenses, and falls into the tray 124. From the tray 124 reactants pass through the opening into the catalyst bed. Product formed in the bed falls into the liquid phase 140, and is removed by a line 142.

CONTINUOUS VPR WITH VAPOR FEED TO CATALYST

Figure 6:
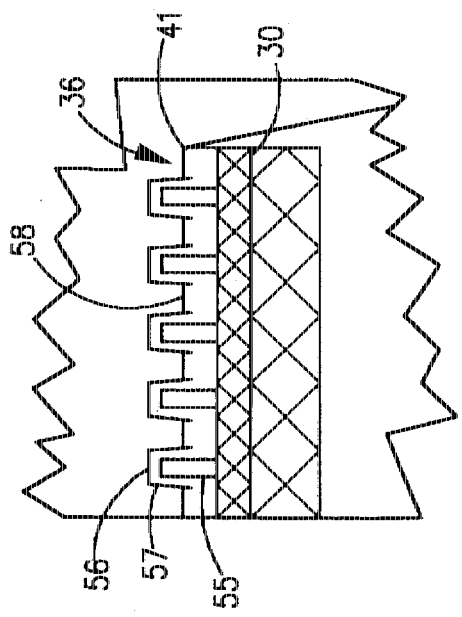
FIG. 6 is an cross-sectional side view of the top bubblecap tray and catalyst bed of the reactor of FIG. 5.
Figure 5:
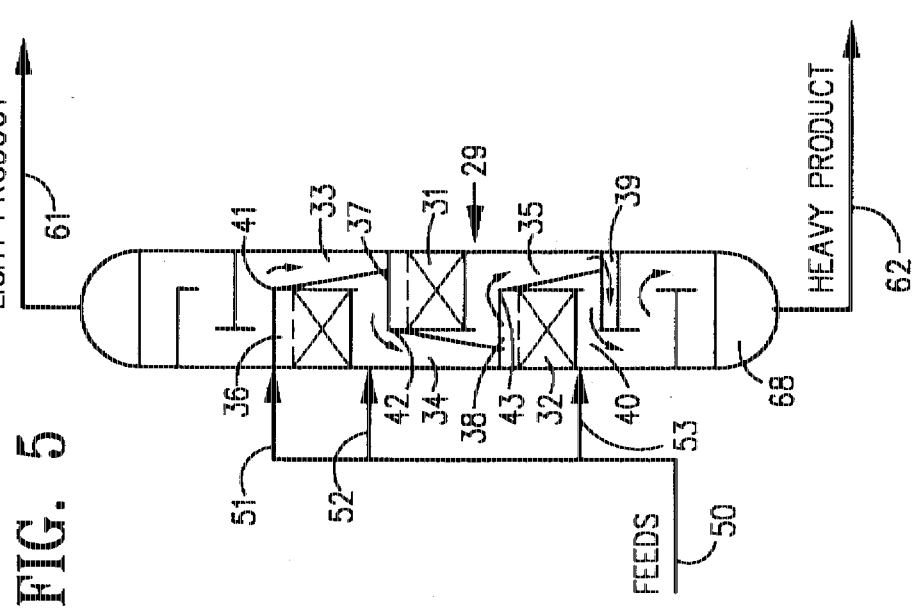
FIG. 5 is a cross-sectional side view of a continuous multi-stage reactor embodiment of the invention with the reactants contacting the catalyst in a vapor state.

With reference to FIG. 5, there is shown a multistage embodiment of a VPR 29 which will accommodate continuous flow to produce large volumes of product. A catalyst bed 30--32 is suspended in the vapor space 38--40 below each of three liquid filled trays 36--38. A downward flowing liquid path is provided between the trays 36--38 by downcomers 33--35, with each downcomer being fed by condensate overflowing a weir 41--43 on each tray. Each tray 36--38 has a "bubble cap" structure as shown in FIG. 6 which comprises a plurality of holes with a cylindrical member 55 about each hole and extending upwardly. Liquid on each tray exits the tray 36 via the weir 41. Each cylindrical member has a cap 56 spaced from the top end thereof. The cap 56 has a skirt 57 portion extending downwardly about the top end of the cylindrical member 55 but spaced therefrom such that vapor passing upwardly through the member is deflected down by the cap 56 and into the liquid 58 on the tray.

The caps 56 prevent the liquid 58 in the tray 36 from flowing down the cylindrical tubes 55 while vapor is rising from the catalyst bed 30 up through the tubes. The caps 56 function to deflect the vapor downwardly in the liquid 58 and bubble therethrough. Hence, the term "bubblecap". Preferably the top of the caps 56 are above the level of the top of the wier 41, and the skirt 57 of each cap extends downwardly into the liquid 58 on the tray 36. Also, the top of each cylindrical tube 55 is preferably at a height slightly above the height of the weir such that the possibility of liquid passing down the cylindrical tubes is further minimized.

The initial direction of travel of the product(s) formed in the catalyst beds is not clear. One possibility is that the product is displaced from the catalyst bed by upwardly flowing vapor which strips each catalyst bed and carries reactants and product into the liquid layer on the tray directly above. The vapor is intimately mixed with the liquid in each tray 36–38, such that the liquid acts as a heat exchanger to remove heat from the vapor and to selectively condense reaction product out from the vapor stream and into the liquid. This selective condensation occurs because the reaction product has a lower vapor pressure than that of the reactants.

Another possibility is that the product made in each catalyst bed falls into the tray below, with the unconverted vapor being contacted with the liquid on the tray above where heat and mass transfers occur. A combination of part of the product being displaced upwardly into the tray above and part of the product falling into the tray below may also happen. However, experiments have not yet clarified whether the product is swept up to the tray above each catalyst bed, falls to the tray below or a combination of both. In any case, the important aspect of the initial direction of the product is that upon exiting a catalyst bed the product enters the downward flowing path as defined by the trays 36–38, weirs 41–43 and downcomers 33–35, and does not again come into contact with catalyst.

Liquid feed is fed to the reactor 29 by a line 50 with branches 51–53 feeding the various vapor spaces where reactants are vaporized from the liquid stream defined by the liquid filled trays 36–39, the downcomers 33–35 to the bottoms liquid product zone. Vapor passing upwardly through the catalyst beds 30–32 flows upwardly through the cylindrical members 55 on the respective tray 36–38 above each catalyst bed 31–32 and prevents downward flow of liquid from the trays. With catalyst beds 30–32 beneath the trays, the catalyst beds are continuously contacted by the upflowing reactants in a vapor phase. The rising vapor is enriched in the reactants, e.g. methanol and iso-olefin that were depleted in the catalyst bed directly below. Unreacted vapor exits the reactor by an overhead line 61.

The vertical temperature profile of the reactor is monitored by a plurality of temperature sensors and the feed rate and/or heat rate applied to the reactor are controlled accordingly. Heat may be applied to the reactor by any of several known systems, such as a steam jacket or reboiler at the lower end 93 of the reactor.

Although this embodiment is described with a bubble cap tray, alternative trays may be used provided they function as a one-way valve permitting upward flow of vapor and preventing downward flow of the liquid on the tray. Other examples are flapper trays and sieve trays.

The reaction in the reactor 29 is not believed to be a gas phase reaction. The vapor phase is at its dew point, and contact with a high surface area catalyst should cause capillary condensation to occur. Thus, even though it is in the vapor space and contacted by vapor, the catalyst can be wetted at all time with liquid condensate. The heat of reaction is removed by the upflowing vapor and is used to help run the distillation. As with the other embodiments of the invention, an advantage of the multistage VPR is that product formed at any catalyst bed is removed from the reactor without any additional catalyst contact. This is very important because of the reversible nature of equilibrium-limited reactions and to prevent the product from entering further forward secondary reactions. Anytime product enters a reaction zone, it has the potential to undergo the highly undesired decomposition reaction to starting materials. This is prevented in the VPR by the low volatility of the product. Once in the liquid phase on any tray, product will flow to the bottom 60 of the VPR via the flow path defined by the trays 36–38, weirs 41–43 and downcomers 33–35 without contacting catalyst. Product is continuously removed from the reactor 28 by a line 62. In comparison, typical known catstill operation inevitably leads to more product reaction as heavy product becomes more concentrated because the condensed product is brought back into contact with the catalyst beds. Furthermore, the reaction temperature also rises in successively lower reaction zones which additionally increases undesirable product reactions.

Depending on the reaction and the catalyst, it should be noted that a very slight fraction of the liquid from the tray below or from the tray above may become entrained in a catalytic zone. However, even in this case essentially all the liquid in the multistage reactor bypasses the catalytic zones.

The benefits of the continuous multi-stage flow VPR shown in FIG. 5 are similar to those of the batch VPR of FIG. 1. For example, the composition of the reactants in each catalyst bed is determined by the composition of the vaporized bulk liquid supplied to the reactor.

The FIG. 5 multi-stage VPR unit is also functionally similar to the batch VPR of FIG. 1 in that pumping of the reactants across the bed is accomplished by reflux, i.e., by cyclic vaporization (boiling) and condensing. In the batch VPR of FIG. 1, the ratio of the weight percent of the feed stock in the liquid phase and in the vapor phase is constant. The composition of the liquid phase changes with time, but the relative amounts of liquid and vapor remain the same. For every gram of liquid that is vaporized there is condensation of a corresponding amount of vapor from the condenser to be returned to the liquid phase. This is reflux and is similar or analogous to moving a stream using a pump.

Figure 7:
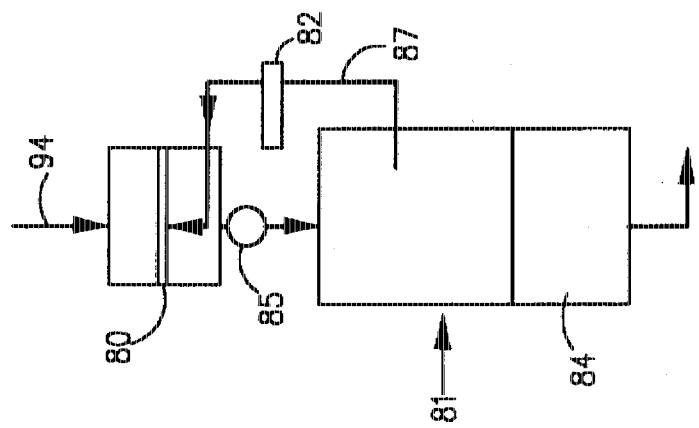
FIG. 7 is another continuous reactor system embodiment, also with the reactants contacting the catalyst bed in a vapor phase.

In an alternative embodiment of FIG. 7, the catalyst bed 82 of FIG. 3 is moved to the vapor pump-around line 87. In this case, reactants are passed through the catalyst bed in a vapor state. Thus, the system of this embodiment functions in a manner similar to that of FIG. 2.

Etherification to make fuel ethers is an important reaction to be carried out in accordance with the VPR systems of present invention. Another important reaction is esterification. Etherification is used to make MTBE, TAME and ethers from the mixed iso-olefins in FCC gasoline. As noted above, the VPR systems of the present invention are suitable for other condensation reactions such as isoparaffin olefin alkylation, the formation of esters for synthetic lubricants and additives such as amides, and oligomerization of olefins, for example isobutylene dimerization. The isobutylene dimer is used as an aromatic alkylate. The systems are also useful in the addition of hydrogen sulfide to olefins make thiols and thioethers, and for hydration reactions such as the addition of water to olefins to make alcohols.

A common element of all of the embodiments of FIGS. 1 though 7 is that the invention improves the productivity of the catalyst systems because the catalyst bed(s) is enriched in more volatile reactants, and depleted of products which are rapidly removed from the catalyst, thus shifting the reaction equilibrium towards the desired condensed products.

EXAMPLES

Table I shows results of $C_5/C_6$ FCC gasoline etherification at equilibrium in the batch VPR of FIG. 1, and compares the results with unmodified, liquid phase autoclave processing wherein the top of the autoclave is open to atmospheric pressure. The feed was 50 g of $C_5/C_6$ FCC gasoline (0.17 moles of etherifiable olefins), 5.55 g of methanol (0.17 moles). The reaction temperature was 190° F. for the batch VPR run and 185° F. for the autoclave run. It should be noted that lower temperature favors MeOH and olefin conversion to ether. 1.5 g of Amberlyst-15 was used as catalyst, and the run time in each case was twenty hours which was sufficient to bring the reactor to equilibrium.

TABLE I

| Etherification | | |
|---|---|---|
| | Autoclave Run | VPR Run |
| % C5 Conversion | 51 | 80 |
| % C6 Conversion | 28 | 60 |
| % MeOH Conversion | 35 | 70 |
| Wt % Ethers | 10 | 20 |

The VPR run outperformed the standard autoclave processing, with methanol and olefin conversion being doubled. The product from the autoclave was 6 wt % methanol, while the product from the VPR was only 3 wt % methanol.

By adjusting the methanol to olefin ratio, the batch VPR of FIG. 1 provides a breakthrough in $C_5+$ etherification, and substantially improves the yields and resultant economics of $C_5$ and $C_6$ olefin etherification. The process of the present invention obtains very high conversions of $C_5+$ iso-olefin. Thus, operation in accordance with the present invention leads to at least a reduction in the size of a methanol recovery unit for removing methanol from the overhead stream of the typical catstill for recycle to the catstill. Optimization of the VPR has the potential to eliminate the need for such a unit.

Further, use of the VPR can eliminate the need for a hydrotreater to pretreat the feed. A typical feed may have about 1% 1,3-butadiene which tends to significantly coke catalyst. In a known process for reacting 1,3-butadiene and isobutylene with methanol using acid catalysis, isobutylene is more reactive than 1,3-butadiene. The process selectively reacts isobutylene to MTBE in the presence of an excess of 1,3-butadiene by operating at high methanol to olefin ratio, e.g., 5:4. However, refinery operators prefer not to operate at high methanol to olefin ratio because such operation would require a relatively large methanol separator and methanol recycle. Therefore, operators prefer to perform selective diene hydrogenation in a hydrotreater to reduce 1,3-butadiene to butene.

The VPR permits the use of a reactant feed stream to the reactor having a methanol to olefin weight ratio as low as 1:1. However, internally the vapor and/or condensate phases would contact the catalyst bed(s) at as high as a 3–4:1 methanol:olefin mole ratio. This methanol enrichment at the catalyst zone prevents or at least minimizes the potential of coking the catalyst by diene oligomerization. Thus, the VPR would be able to process the 1,3-butadiene and isobutylene reaction without the need for a hydrotreater to perform the hydrogenation step.

The VPR shifts the apparent equilibrium of equilibrium-limited reactions in which the boiling point of the product is higher than the boiling point of the reactants. A specific case is the formation of TAME from the reaction of isoamylene with methanol.

Figure 8:
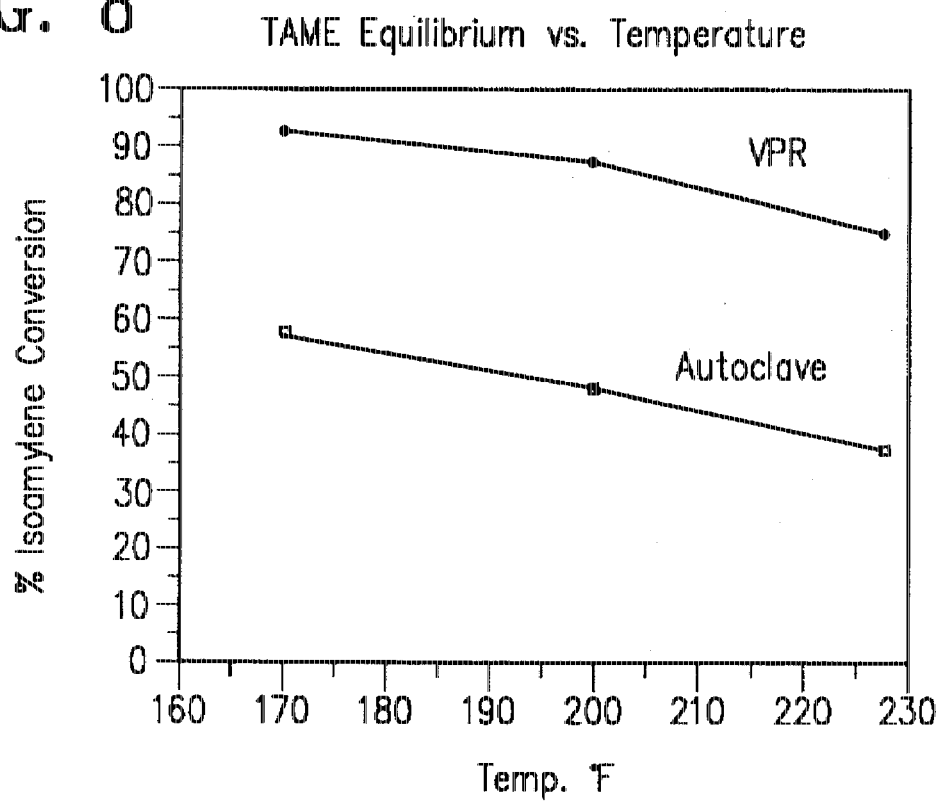
FIG. 8 are curves of equilibrium conversion reactions vs. temperature in the reactor of FIG. 1 and in a laboratory autoclave.

FIG. 8 shows a plot of equilibrium isoamylene conversion vs. temperature in each of the batch VPR of FIG. 1 and the laboratory autoclave at a methanol:isoamylene feed weight ratio of 1.25. The FIG. 8 plots demonstrate that the VPR of FIG. 1 approximately doubles equilibrium conversion of isoamylene to TAME over the temperature range of 170° F. to 225° F.

The catalyst brings the surrounding reaction mixture to equilibrium. The reason TAME production is doubled in the VPR compared to a regular autoclave is that the surrounding reaction mixture in the VPR is methanol rich and TAME poor. This is because in the VPR the reaction mixture surrounding the Amberlyst-15 is condensed vapor, which has a very different composition from the bulk reaction mixture that surrounds Amberlyst-15 in the standard autoclave runs. This is demonstrated by the data in the following Tables 2 and 3.

In the following examples, methanol (Baker), isoamylene (Aldrich), hexane (Aldrich), and Amberlyst-15 (Rohm and Haas) were used without further purification. Amberlyst-15 was refluxed in 3 gm of methanol per gm of catalyst for 1 hour and then filtered and dried overnight at 120° C. A 25 wt % isoamylene, 25 wt % n-pentane, 14 wt % methanol, and 37 wt % n-hexane feedstock was formulated. The paraffins were included as unreactive internal standards. This near stoichiometric ratio (1.25 moles methanol per mole isoamylene) was chosen because of its commercial relevance. 0.25 gm of Amberlyst-15 was used to convert 81.5 gm feedstock in a side-by-side comparison of the VPR of FIG. 1 (Amberlyst-15 in the vapor space) with a regular autoclave (Amberlyst-15 in the liquid). The experiments were run until the composition by GC remained constant, indicating that equilibrium had been reached.

Four blends were prepared and examined to determine the differences in composition between the solution and vapor phases in the VPR which are listed in Table 2. Each blend (250 gm) was placed into a 600 ml VPR without catalyst and brought to 230° F. The liquid and vapor were sampled alternately and analyzed by GC to determine compositions shown in Table 3. Table 4 provides ratios of concentrations in Tables 2 and 3. The last two columns in Table 4 provide the relative enrichment of methanol vs isoamylene in the reaction zone and the relative depletion of TAME vs. isoamylene in the reaction zone, respectively.

TABLE 2

| Liquid Phase Compositions | | | | | | |
|---|---|---|---|---|---|---|
| Blend | MeOH | Isoamylene | TAME | Pentane | Hexane | Total |
| A | 12.5 | 24.3 | 0.0 | 24.7 | 38.5 | 100.0 |
| B | 8.6 | 22.4 | 0.0 | 21.1 | 47.9 | 100.0 |
| C | 4.8 | 13.4 | 24.8 | 13.2 | 43.8 | 100.0 |
| D | 1.6 | 13.6 | 26.2 | 13.6 | 45.1 | 100.0 |

TABLE 3

| Vapor Phase Compositions | | | | | | |
|---|---|---|---|---|---|---|
| Blend | MeOH | Isoamylene | TAME | Pentane | Hexane | Total |
| A | 19.8 | 29.3 | 0.0 | 33.1 | 17.8 | 100.0 |
| B | 23.2 | 26.5 | 0.0 | 28.3 | 22.0 | 100.0 |

TABLE 3-continued

Vapor Phase Compositions

| Blend | MeOH | Isoamylene | TAME | Pentane | Hexane | Total |
|---|---|---|---|---|---|---|
| C | 22.6 | 23.0 | 5.2 | 26.8 | 22.4 | 100.0 |
| D | 14.8 | 26.5 | 6.0 | 29.6 | 23.1 | 100.0 |

TABLE 4

Ratios

| Blend | MeOH Vapor / MeOH Liquid | TAME Vapor / TAME Liquid | Isoamylene V / Isoamylene L | M/A-V[a] / M/A-l | T/A-V[b] / T/A-L |
|---|---|---|---|---|---|
| A | 1.6 | --- | 1.2 | 1.4 | --- |
| B | 2.7 | --- | 1.2 | 2.3 | --- |
| C | 4.7 | 0.21 | 1.7 | 2.7 | 0.16 |
| D | 9.2 | 0.23 | 2.0 | 5.0 | 0.16 |

[a]Methanol to isoamylenes mole ratio in the vapor phase divided by the same ratio in the liquid phase.
[b]TAME to isoamylenes mole ratio in the vapor phase divided by the same ratio in the liquid phase.

Figure 9:
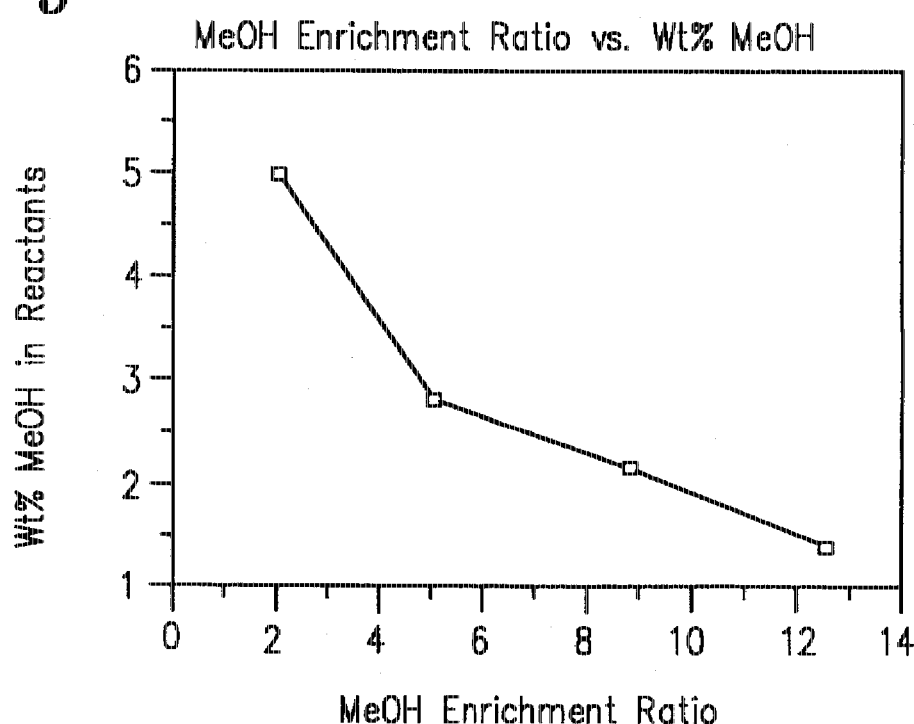
FIG. 9 is a plot of the methanol enrichment ratio vs. weight percent of methanol in the reactants of FIG. 1.

FIG. 9 is a plot of the methanol enrichment ratio (wt % MeOH in vapor/wt % MeOH in liquid) vs. wt % methanol in the liquid phase, and demonstrates a dependence of methanol enrichment upon methanol concentration. The reason for this dependence is the highly nonideal character of methanol/hydrocarbon solutions. Unlike TAME/hydrocarbon solutions, the vapor composition above nonideal methanol/hydrocarbon solutions cannot be predicted using Raoult's Law. Less methanol in solution means less hydrogen bonding, and higher relative methanol vapor pressure. This exactly what is needed to drive the reaction equilibrium towards TAME. As TAME is formed, the methanol concentration in the bulk liquid drops, and the vapor phase enrichment ratio rises.

Figure 10:
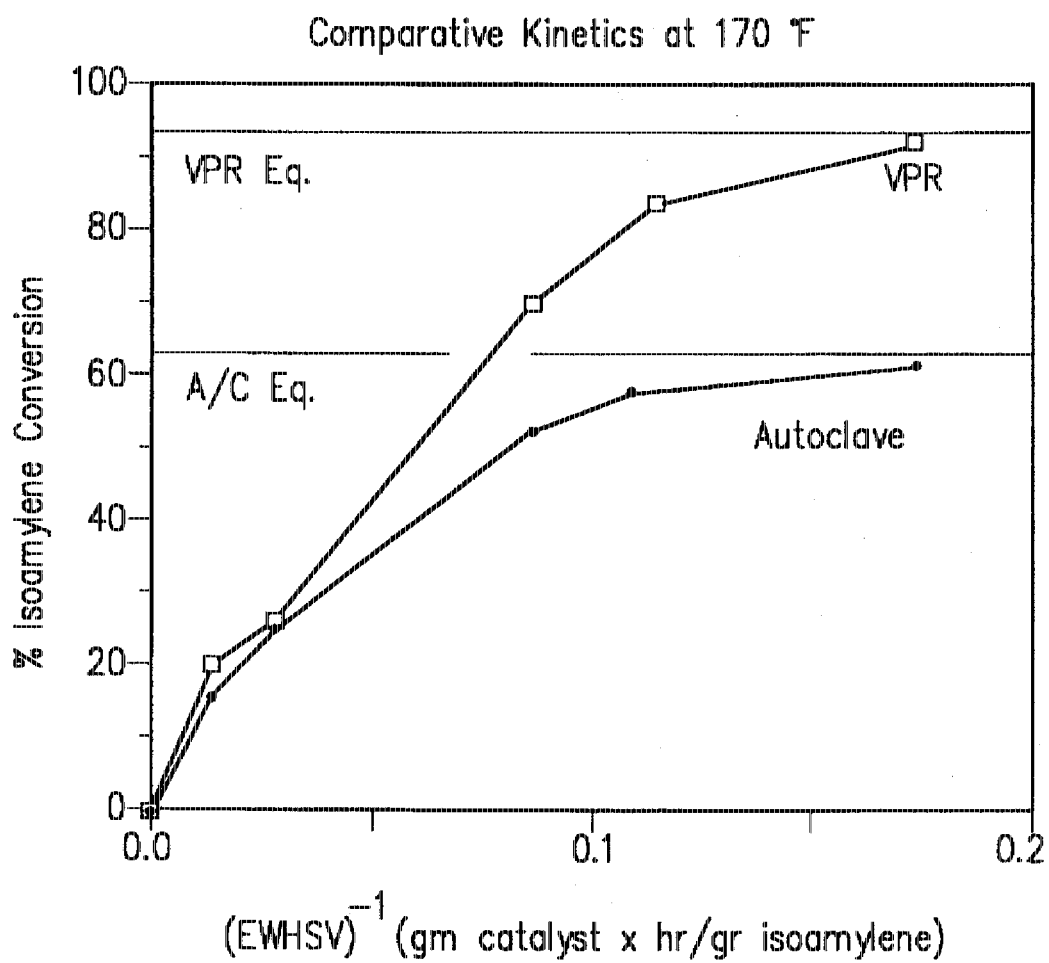
FIG. 10 are plots of percent conversion vs. contact time for the reactor of FIG. 1, and of a laboratory autoclave for TAME synthesis.

With the data in Tables 2–4 and FIG. 9, the composition of the catalyst zone in a VPR TAME reaction can be calculated from the composition of the bulk reaction mixture. As stated above, the condensate is enriched in methanol and depleted in TAME relative to the bulk liquid which shifts equilibrium conversion in favor of TAME production. As shown in FIG. 10, at equilibrium at 170° F. the VPR achieves 92 wt % isoamylene conversion vs. 58 wt % for the autoclave. The VPR does not stop at 58% isoamylene conversion because when both reactors have reached that point, the methanol:isoamylene:TAME mole ratio surrounding the catalyst in the autoclave is ca. 3:2:2 while in the VPR the same ratio calculated from the data in Tables 2–4 is ca. 30:8:1. At equilibrium in the VPR, the mole ratio changes to ca. 6:1:2. TAME becomes an important component of the equilibrium condensate in the VPR because the reactants have nearly completely converted.

The kinetics of the VPR of FIG. 1 and of a typical autoclave were investigated at 170° F., a typical temperature for commercial TAME synthesis. The graphs of FIG. 10 show that both the VPR and the autoclave reach respective equilibriums after identical contact times, the x-axis being space time. The horizontal lines at about 62% and about 92% conversion are the equilibrium conversion for the autoclave (A/C) and the VPR reactions, respectively. The VPR has a kinetic advantage because the continuous removal of TAME from the reaction zone reduces reverse reaction. Thus, FIG. 10 demonstrates the increase in productivity of the batch VPR embodiment of FIG. 1 over a typical laboratory autoclave. This increase in productivity is unexpected because of the lower concentration of moles of reactants in the vapor relative to the liquid.

As discussed above, product protection is another general advantage of the VPR. In many chemical reactions in known catstills, selectivity at low conversion is excellent, but at higher conversions selectivity drops due to secondary reactions of the desired kinetic products. In the VPR, higher boiling products are effectively removed from the reaction zone upon their formation. Due to their higher boiling points, the products remain in the bulk solution where no secondary reactions can occur because the bulk solution does not contact the catalyst. The reaction zone is enriched in reagents and depleted in products.

IPA Conversion to DIPE

Amberlyst-15 was treated overnight in a soxhlet extractor with refluxing methanol. It was then dried at 212° F. overnight and stored for use without further treatment. A commercial acidic catalyst in an extrudate comprising 70 wt % Beta and 30 wt % $ZrO_2$ binder (Zirconia) zeolite was used with no pretreatment.

Figure 11:
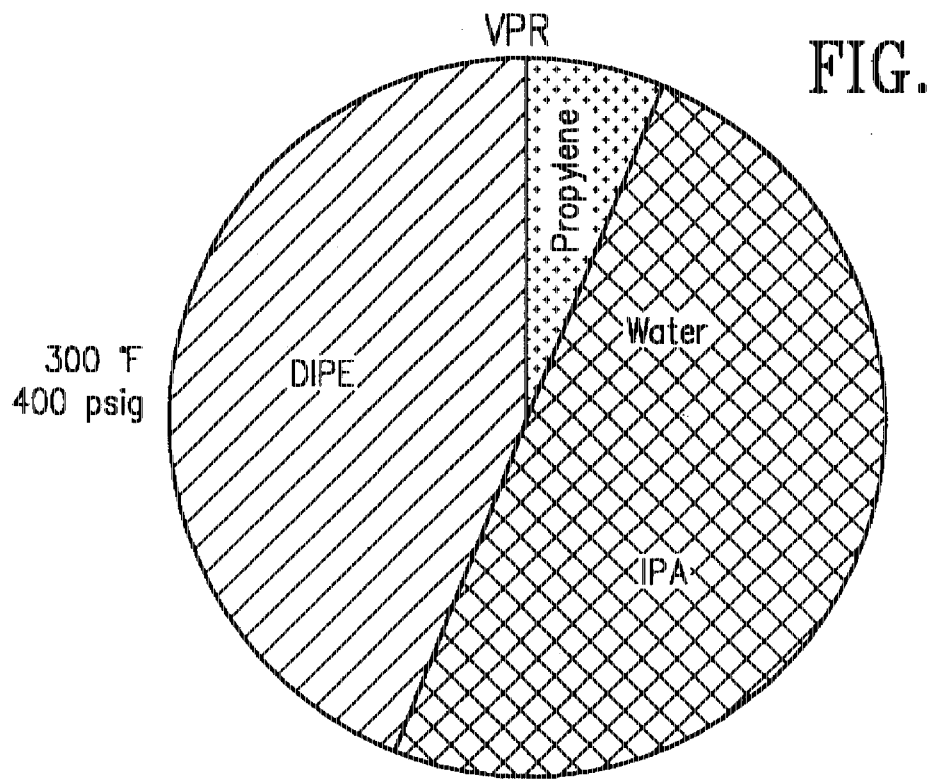
FIG. 11 is a graph of product distribution from reaction of IPA to DIPE synthesis in the FIG. 1 reactor.

A 450 cc VPR was loaded with 150 gms IPA and 5 gms of the above treated Amberlyst-15. An identical experiment was run substituting 5 gms of the Beta catalyst for the Amberlyst-15. In each case, the VPR was sealed and briefly evacuated using house vacuum. The VPR was then heated to 300° F., and compressed air was blown rapidly though the condenser. These conditions were maintained for 48 hrs. Prior experiments showed that beyond 48 hrs, increasing contact time did not change the product composition as determined by GC. Thus, 48 hrs is sufficient to bring the reaction to equilibrium. The VPR was then cooled and the reactor contents analyzed yielding the product distribution shown in FIG. 11. As expected, the same product distribution was obtained with both catalysts indicating that these conditions achieved equilibrium.

Figure 12:
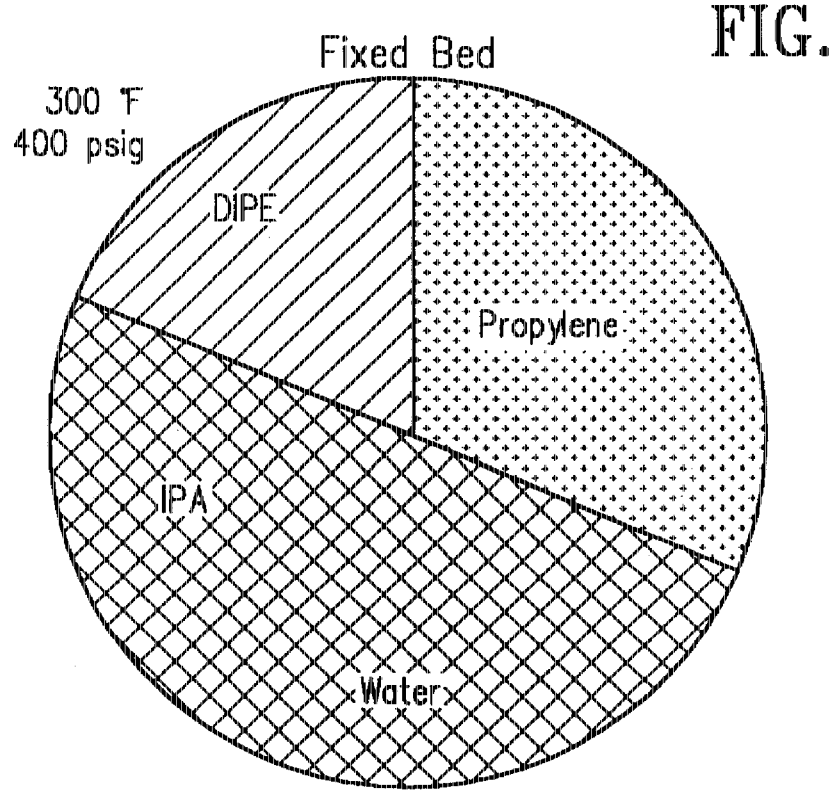
FIG. 12 is a graph of product distribution from reaction of IPA to DIPE in a conventional fixed bed reactor.

Fixed bed equilibrium results were obtained as follows. A 12 inch length, 0.5 inch diameter reactor was loaded with 10 gms of the above treated Amberlyst-15 catalyst. It was sealed and pressure tested. IPA was delivered to the reactor with a Milton Roy pump at varying rates until the composition of the product stopped changing with changes in rate (at 5 gm/hr). The total product stream was passed though a condenser held at 10° F. The gas stream passed through a backmixer, a sample bomb, and a gas meter. The product distribution is shown in FIG. 12. Thus, the VPR shifts equilibrium producing a higher yield of desired DIPE product.

Isobutylene Dimerizations

Figure 13:
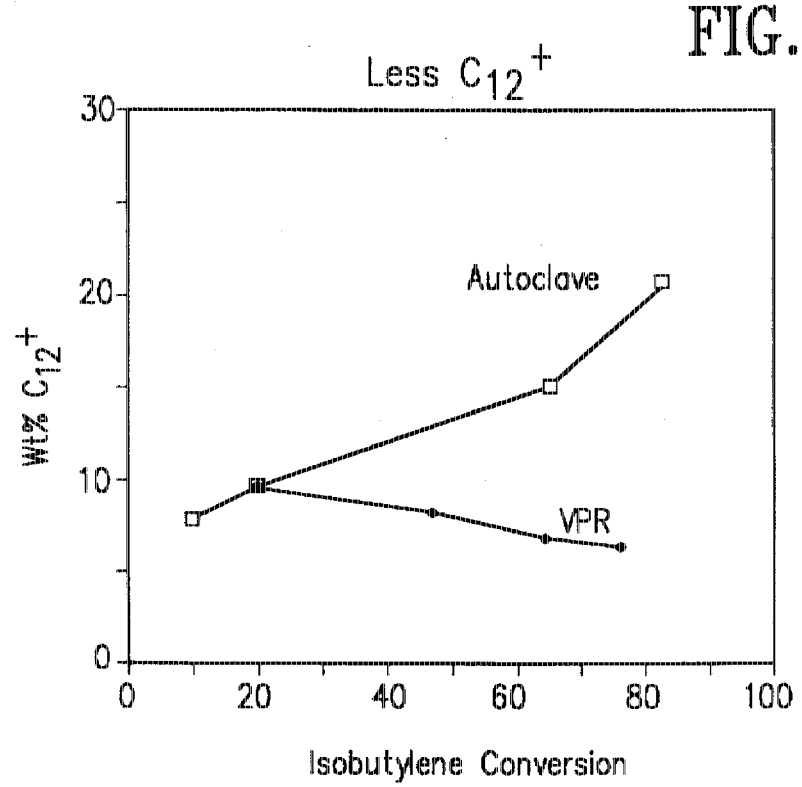
FIGS. 13 and 14 are graphs of isobutylene conversion reactions in the reactor of FIG. 1 and in a laboratory autoclave.
Figure 14:
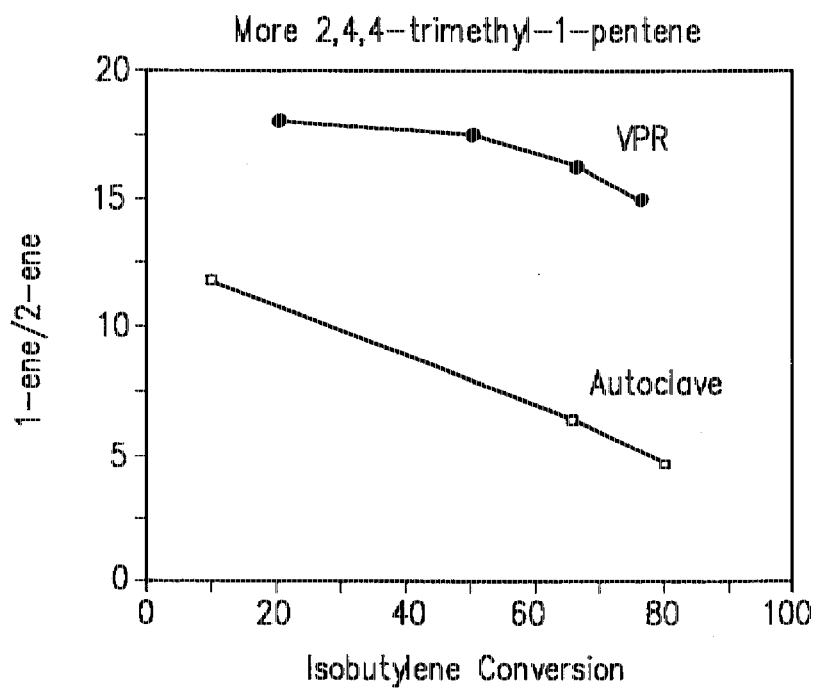

A 450 cc VPR was evacuated and then loaded with 90 gms isobutylene and 5 gms of the above described Beta catalyst. The reactor was heated to 140° F. and held there for 4 hours while a slow steady stream of tap water was flowed through the condenser. Then the reactor was cooled to room temperature. The entire contents of the reactor were transferred to a hoke vessel. This was sampled with a high pressure syringe and analyzed by GC. The products were characterized only as dimers and oligomers. There were only two dimers formed, 2,4,4-trimethyl-1-pentene and 2,4,4-trimethyl-2-pentene. This experiment was repeated except the reactor was held at 140° F. for 8, 12, and 16 hours. The product composition and dimer selectivity are shown in FIGS. 13 and 14 on the VPR lines.

The above experiments were then repeated at 4,12 and 16 hours in a standard laboratory autoclave where the catalyst is stirred in the liquid phase. The product composition and dimer selectivity is given in FIG. 13 and 14 on the autoclave lines. The VPR improved the selectivity of this reaction by preventing secondary reaction of the kinetic product 2,4,4-trimethyl -1-pentene. Both reactions with isobutylene (monomer) to form oligomer and isomerization to form 2,4,4-trimethyl -2-pentene are prevented.

CATALYSTS

Catalyst useful for MTBE and TAME processes in the VPR are any one of solid acid catalysts, such as sulphonated polystyrene resins ($H_2SO_4$ fixed on polymer) or zeolites. Other suitable catalyst are noted above in the description of the prior art. Obviously, the catalyst used in a specific process is determined by the reaction process contemplated. One would first identify the process and then use whatever catalyst is needed for that particular process.

Catalyst suitable for the MTBE or TAME processes are cation exchange resins which contain sulfonic acid groups, and which have been obtained by polymerization or copolymerization of aromatic vinyl compounds followed by sulfonation. Examples of aromatic vinyl compounds suitable for preparing polymers or copolymers are styrene, vinyl toluene, vinyl naphthalene, vinyl ethylbenzene, methyl styrene, vinyl chlorobenzene and vinyl xylene. There are a large number of methods used for preparing these polymers. For example, polymerization, alone or in admixture with other monovinyl compounds, or by crosslinking with polyvinyl compounds such as divinyl benzene, divinyl toluene, divinylphenyl ether and others. The polymers may be prepared in the presence of absence of solvents or dispersing agents. Also, various polymerization initiators may be used, e.g., inorganic or organic peroxides, persulfates, and the like.

The sulfonic acid group may be introduced into these vinyl aromatic polymers by various known methods, such as, by sulfating the polymers with concentrated sulfuric acid or chlorosulfonic acid, or by copolymerizing aromatic compounds which contain sulfonic acid groups (see e.g., U.S. Pat. No. 2,366,007). Further sulfonic acid groups may be introduced into these polymers which already contain sulfonic acid groups, for example, by treatment with fuming sulfuric acid, i.e., sulfuric acid which contains sulfur trioxide. The treatment with fuming sulfuric acid is preferably carried out at 0° C. to 150° C. and the sulfuric acid should contain sufficient sulfur trioxide after the reaction. The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1% to 20% by weight of the copolymer (see, e.g., German Patent Specification No. 908,247).

The ion exchange resin is preferably used in a granular size of about 0.25 to 1 mm, although particles from 0.15 mm up to about 1 mm may be employed. The faster catalysts provide high surface area, but also result is high pressure drops through the reactor. The macroreticular form of these catalysts is preferred because of the much larger surface area exposed and the limited swelling which all of these resins undergo in a nonaqueous hydrocarbon medium.

Similarly, other acid resins are suitable, such as perfluorosulfonic acid resins which are copolymers of sulfonyl fluorvinyl ethyl and fluorocarbon and described in greater detail in DuPont "Innovation", Volume 4, No. 3. Spring 1973 or the modified forms thereof as described in U.S. Pat. Nos. 3,784,399, 3,770,567 and 3,849,243. Cation exchange resin structures prepared by the process described in U.S. Pat. No. 4,250,052, may also be employed.

Other suitable catalysts are $H_3PO_4$ on Kieselguhr, $AlCl_3$, $ZrO_2$-$H_2SO_4$, $BF_3$-$SiO_2$, $AlCl_2/SiO_2$, $MgO_2$ (base) and Nafion-4 (Rohm & Haas).

The acidic zeolite catalyst which can be used in condensation reaction such as MTBE or TAME processes in accordance with the present invention comprises an acidic zeolite in combination with a binder or matrix material such as alumina, silica, or silica alumina. The preferred zeolites for use in the catalysts of the present process are the medium pore size zeolites, especially those having the structure of ZSM-5, ZSM-11, ZSM-12, ZSM-22, ZSM-23, ZSM-35, ZSM-48, MCM-22, mordenite, ferrierite, and zeolite L. The medium pore size zeolites are a well-recognized class of zeolites and can be characterized as having a Constraint Index of 1 to 12. Constraint Index is determined as described in U.S. Pat. No. 4,016,218 incorporated herein by reference. Catalysts of this type are described in U.S. Pat. Nos. 4,827,069 and 4,992,067 which are incorporated herein by reference and to which reference is made for further details of such catalysts, zeolites and binder or matrix materials.

The present process may also use catalysts based on large pore size zeolites such as the synthetic faujasites, especially zeolite Y, preferably in the form of zeolite USY. Zeolite beta may also be used as the zeolite component. Other materials of acidic functionality which may be used in the catalyst include the materials identified as ZSM-20, MCM-36 (described in U.S. patent application Ser. No. 07/811,360, filed 20 Dec., 1991) and MCM49 (described in U.S. Pat. No. 5,236,575). The application and the patent describing MCM-36 and MCM-49, respectively, are incorporated herein by reference.

Thus, the preferred acidic zeolite catalysts are those exhibiting high alpha activity and having a zeolite structure of ZSM-5, ZSM-11, ZSM-12, ZSM-20, ZSM-22, ZSM-23, ZSM-35, ZSM-48, MCM22, MCM-36, MCM-49, zeolite Y, zeolite beta, mordenite, ferrierite and zeolite L.

The Alpha Test is described in U.S. Pat. No. 3,354,978, and the Journal of Catalysis, Vol. 4, pg. 527 (1965); Vol. 6, pg. 278 (1966); and Vol. 61, pg. 395 (1980), each incorporated herein by reference as to that description.

ZSM-5 crystalline structure is readily recognized by its x-ray diffraction pattern, which is described in U.S. Pat. No. 3,702,866. ZSM-11 is disclosed in U.S. Pat. No. 3,709,979, ZSM-12 is disclosed in U.S. Pat. No. 3,832,449, ZSM-22 is disclosed in U.S. Pat. No. 4,810,357, ZSM-23 is disclosed in U.S. Pat. Nos. 4,076,842 and 4,104,151, ZSM-35 is disclosed in U.S. Pat. No. 4,016,245, ZSM-48 is disclosed in U.S. Pat. No. 4,375,573 and MCM-22 is disclosed in U.S. Pat. No. 4,954,325. The U.S. Patents identified in this paragraph are incorporated herein by reference.

While suitable zeolites having a coordinated metal oxide to silica molar ratio of 20:1 to 200:1 or higher may be used, it is advantageous to employ aluminosilicate ZSM-5 having a silica:alumina molar ratio of about 25:1 to 70:1, suitably modified. A typical zeolite catalyst component having Bronsted acid sites may consist essentially of crystalline aluminosilicate having the structure of ZSM-5 zeolite with 5 to 95 wt.% silica, clay and/or alumina binder.

These siliceous zeolites are employed in their acid forms, ion-exchanged or impregnated with one or more suitable metals, such as Ga, Pd, Zn, Ni, Co and/or other metals of Periodic Groups III to VIII. The zeolite may include other components, generally one or more metals of group IB, IIB, IIIB, VA, VIA, or VIIIA of the Periodic Table (IUPAC).

Useful hydrogenation components include the noble metals of Group VIIIA, especially platinum, but other noble metals, such as palladium, gold, silver, rhenium or rhodium, may also be used. Base metal hydrogenation components may also be used, especially nickel, cobalt, molybdenum, tungsten, copper or zinc.

The catalyst materials may include two or more catalytic components which components may be present in admixture or combined in a unitary multifunctional solid particle.

In addition to the preferred aluminosilicates, the gallosilicate, ferrosilicate and "silicalite" materials may be employed. ZSM-5 zeolites are particularly useful in the process because of their regenerability, long life and stability under the extreme conditions of operation.

In the fixed bed embodiments of the present invention the catalyst may consist of a standard 70:1 aluminosilicate H-ZSM-5 extrudate having an alpha value of at least 20, preferably 150 or higher.

Suitable pressure for the embodiments of FIGS. 1 to 7 range from about zero absolute to about 10,000 psig, preferably from about zero absolute to about 2,000 psig, and more preferably from about zero absolute to about 1,000 psig. Low pressure, specifically zero absolute pressure, is significant because if one wants to use a condensation reaction with a high molecular weight material such as an octadecene ($C_{18}$) olefin and dimerize or condense it to $C_{36}$ olefin, either of VPR units of FIGS. 1 to 7 would require working at very low pressure and preferable in a near zero absolute range to vaporize the feed.

Conversely, if one was to condense a very low molecular weight feed such as ethylene having an ambient vapor pressure of about 800 psig to an oligomer of a desired molecular weight, it would be necessary to operate the VPR above 800 psig, and might well need to operate in excess 2000 psig.

As discussed hereinabove, the pressure is tied to the temperature. For example, temperatures for MTBE and TAME reactions are in the range of from about 120° F. to about 400° F., and preferably from about 140° F. to about 180° F. Pressure is proportional to temperature, and inversely proportional to reactant molecular weight. Specifically, low molecular weight reactants and high reaction temperature require high or highest pressures. Conversely, high molecular weight reactants and low reaction temperatures call for lower or lowest pressures. Although the disclosed embodiments couple pressure and temperature, decoupling the pressure and temperature is also contemplated by this invention.

The preferred WHSV for the TAME and MTBE processes ranges from about 0.1 to about 10.0 $hr^{-1}$, and preferably from about 0.5 to about 2.0 $hr^{-1}$.

As used herein "bulk separation" means separation of a batch or continuous feedstream by a catalytic reaction process into multiple output or product steams such as occurs in prior art catstills, in a typical autoclave batch reactor and in the above described FIG. 5 embodiment.

Although the embodiments of FIGS. 1 to 4 and 7 have internal flow or stream separations, each system processes a single feedstream into a single output or product steam, and therefore does not provide separation.

While the invention has been described in conjunction with specific embodiments thereof, it is evident that many alternatives, modifications, and variations will be apparent to those skilled in the art in light of the foregoing description. Accordingly, it is intended to embrace all such alternatives, modification, and variations as fall within the spirit and broad scope of the appended claims.

What is claimed is:

1. A reaction process for converting in a closed reactor at least one reactant to at least one reaction product having a vapor pressure less than the vapor pressure of each of said at least one reactant, said process comprising the steps of:

heating in said reactor a liquid phase comprising said at least one reactant to partial vaporization thus forming a vapor phase of said at least one reactant;

passing said at least one reactant of said vapor phase in a vapor and/or condensed state through at least one catalyst bed spaced in said reactor from said liquid phase for converting said at least one reactant of said vapor phase to said at least one reaction product; and returning said at least one reaction product from said at least one catalyst bed to said liquid phase without additional contact with catalyst.

2. The process of claim 1 further comprising continuing reflux of said at least one reactant between said liquid phase and said vapor phase until a desired concentration of said at least one product is in said liquid phase.

3. The process of claim 1 wherein said at least one reactant of said vapor phase is condensed to liquid prior to contacting said at least one catalyst bed.

4. The process of claim 1 wherein said vapor phase of said at least one reactant passes through said at least one catalyst bed, and said at least one reaction product is condensed prior to being returned to said liquid phase.

5. The process of claim 1 wherein said process is a reversible catalytic etherification process for converting volatile isoalkene and alkanol reactants, and wherein said at least one reaction product is an ether product.

6. The process of claim 5 wherein said isoalkene comprises isobutene, said alkanol comprises methanol, and said ether product comprises methyl tertiary butyl ether.

7. The process of claim 5 wherein said isoalkene comprises isoamylene, said alkanol comprises methanol, and said ether product comprises tertiary amyl methyl ether.

8. The process of claim 1 wherein said process is a MTBE or TAME process, and wherein said at least one catalyst bed includes cation exchange resins which contain sulfonic acid groups obtained by polymerization or copolymerization of aromatic vinyl compounds followed by sulfonation.

9. The process of claim 1 wherein said process is a MTBE or TAME process, and wherein said at least one catalyst bed comprises $H_3PO_4$ on Kieselguhr, $AlCl_3$, $ZrO_2$-$H_2SO_4$, $BF_3$-$SiO_2$, $AlCl_2/SiO_2$, $MgO_2$ (base), Nafion-4, or combimations thereof.

10. The process of claim 2 wherein said process is a MTBE or TAME process, and wherein said at least one catalyst bed includes ZSM-5, ZSM-11, ZSM-12, ZSM-22, ZSM-23, ZSM-35, ZSM-48, MCM-22, mordenite, ferrierite, or combinations thereof.

11. The process of claim 1 wherein said process is a MTBE or TAME process, and wherein said at least one catalyst bed includes zeolite Y, beta, ZSM-20, MCM-36, MCM-49, or combinations thereof.

12. The process of claim 1 wherein said liquid phase comprises methanol and olefins in a mole ratio of about 1:1, and wherein said vapor phase comprises methanol and olefins in a mole ratio of from about 3:1 to about 4:1.

13. The process of claim 1 wherein said vapor phase has a methanol to olefins mole ratio greater than that of the reactants.

14. The process of claim 1 wherein pressure at said catalyst bed is proportional to desired reaction temperature and inversely proportional to the molecular weight of the reactants.

15. The process of claim 1 wherein a quantity said liquid phase of reactants is placed in a bottom portion of a closed vessel, a catalyst bed is spaced above said reactants and a condenser is positioned above said catalyst bed, and wherein said vapor phase passes upwardly around said catalyst bed to said condenser, said condenser transforming said vapor phase reactants to condensate, said condensate passing through said catalyst bed for producing said reaction product, and said reaction product exiting said catalyst bed and falling to said liquid phase, said heating step being continued to reflux the reactants between said liquid phase and said vapor phase until a desired concentration of said product is in said liquid phase.

16. A reactor for converting at least one reactant to at least one reaction product having a vapor pressure less than the vapor pressure of said at least one reactant comprising:

means for heating a liquid phase comprising said at least one reactant to partial vaporization thus forming a vapor phase of said at least one reactant;

means including at least one catalyst bed spaced from said liquid phase for converting the at least one reactant of said vapor phase to said at least one reaction product;

means for passing the at least one reactant of said vapor phase in a vapor and/or condensed state through said at least one catalyst bed; and means for returning said at least one product to said liquid phase without additional contact with catalyst.

17. The reactor of claim 16 further comprising means for controlling reflux of reactants between said liquid phase and said vapor phase until a desired concentration of said at least one product is in said liquid phase.

18. The reactor of claim 16 wherein each of said catalyst beds is supported by a foraminous horizontal support.

19. The reactor of claim 16 wherein each of said at least one catalyst bed is supported by a screen structure.

20. The reactor of claim 16 wherein each of said at least one catalyst bed is formed of an array of permeable plates.

21. The reactor of claim 16 wherein said converting means comprises a plurality of condensation trays vertically spaced in said reactor, and one of the catalyst beds suspended beneath each one of said trays.

22. The reactor of claim 21 wherein said passing means comprises one-way means on each one of trays for permitting flow of said vapor phase upwardly from the catalyst bed therebelow and for preventing liquid flow downwardly from the tray to the catalyst bed.

23. The reactor of claim 22 wherein said returning means comprises means serially connecting said trays for providing a liquid path from the top tray to the bottom tray without contacting the catalyst beds.

24. The reactor of claim 16 wherein said passing means comprises a source of makeup feed, a makeup feed preheater connected to said source, a conduit interconnecting said preheater and a location in said reactor between said catalyst bed and said liquid phase, and means interconnecting said preheater and said reactor above said catalyst bed for maintaining a positive pressure on the upper portion of said catalyst bed, whereby said positive pressure means forms a loop by forcing vapor into said conduit, through said preheater where a minor portion of makeup feed is admixed therewith, into said reactor, downwardly through said catalyst bed for conversion to said at least one product, said product condenses and falls into said liquid phase, and said vapor returns to said conduit.

25. The reactor of claim 16 which includes a liquid phase comprising reactants in a bottom portion of the reactor, a catalyst bed spaced above said bottom portion of said reactor containing said liquid phase, a tray above said catalyst bed, an opening is formed in said tray to said catalyst bed, a pump for pumping liquid through said opening in said tray to said catalyst bed, a condenser positioned above said tray, and a source of fresh feed above said condenser, and wherein said vapor phase passes upwardly around said catalyst bed to said condenser, said condenser transforming said vapor phase reactants to condensate, said condensate passing through said catalyst bed for producing said reaction product, and said reaction product existing said catalyst bed and falling to said liquid phase.

26. The reactor of claim 16 wherein said passing means comprises a source of makeup feed, a makeup feed preheater connected to said source, a conduit interconnecting said preheater and said reactor above and said liquid phase, said catalyst bed being located in said conduit, and means interconnecting said preheater and the upper portion of said reactor for maintaining a positive pressure therein, whereby said positive pressure means forms a loop by forcing vapor into said conduit, through said catalyst bed for conversion to said at least one product, into said preheater where a minor portion of makeup feed is admixed with said at least one product, into said reactor, wherein said product condenses and falls into said liquid phase, and said vapor returns to said conduit.

* * * * *

UNITED STATES PATENT AND TRADEMARK OFFICE
CERTIFICATE OF CORRECTION

PATENT NO. : 5,714,640

DATED : February 3, 1998

INVENTOR(S) : Weldon K. Bell et al.

It is certified that error appears in the above-identified patent and that said Letters Patent is hereby corrected as shown below:

In the Claims:

Column 18, line 59, "claim 2" should read —claim 1—; and
Column 18, line 62, after "ferrierite," insert —zeolite L—.

Signed and Sealed this

Fourteenth Day of July, 1998

*Attest:*

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO. : 5,714,640
DATED : February 3, 1998
INVENTOR(S) : Weldon K. Bell, et al.

It is certified that error appears in the above-identified patent and that said Letters Patent is hereby corrected as shown below:

Column 20, line 37, change "existing" to --exiting--.

Signed and Sealed this

Seventeenth Day of November, 1998

Attest:

BRUCE LEHMAN

Attesting Officer

Commissioner of Patents and Trademarks